(12) United States Patent
Kang et al.

(10) Patent No.: US 10,617,622 B2
(45) Date of Patent: Apr. 14, 2020

(54) HAIR RESTORATION AND/OR HAIR GROWTH PROMOTING COMPOSITION CONTAINING SOYASAPONIN

(71) Applicant: AMOREPACIFIC CORPORATION, Seoul (KR)

(72) Inventors: Young Gyu Kang, Yongin-si (KR); Jae Young Ko, Yongin-si (KR); Jun Seong Park, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 15/764,625

(22) PCT Filed: Sep. 29, 2016

(86) PCT No.: PCT/KR2016/010893
§ 371 (c)(1),
(2) Date: Mar. 29, 2018

(87) PCT Pub. No.: WO2017/057910
PCT Pub. Date: Apr. 6, 2017

(65) Prior Publication Data
US 2018/0303737 A1    Oct. 25, 2018

(30) Foreign Application Priority Data

Sep. 30, 2015    (KR) .................. 10-2015-0137532

(51) Int. Cl.
*A61K 8/60* (2006.01)
*A61Q 7/00* (2006.01)
*A61K 8/63* (2006.01)
*A61K 31/704* (2006.01)
*A61K 8/9789* (2017.01)
*A61Q 19/00* (2006.01)
*A61K 8/02* (2006.01)

(52) U.S. Cl.
CPC .................. *A61K 8/60* (2013.01); *A61K 8/63* (2013.01); *A61K 8/9789* (2017.08); *A61K 31/704* (2013.01); *A61Q 7/00* (2013.01); *A61K 8/02* (2013.01); *A61Q 19/00* (2013.01)

(58) Field of Classification Search
None
See application file for complete search history.

(56) References Cited

FOREIGN PATENT DOCUMENTS

| JP | 07-132064 | 5/1995 |
|---|---|---|
| JP | 2012-031132 | 2/2012 |
| KR | 10-0616342 | 8/2006 |
| KR | 10-2014-0039809 | 4/2014 |

OTHER PUBLICATIONS

"Derivative", Merriam-Webster OnLine Dictionary, http://www.merriam-webster.com/dictionary/derivative (Year: 2009).*
Jeon, H. et al., Korean J. Food Sci. Technol., "Hair Growth Promoting Effect of Black Soybean Extract In Vitro and In Vivo", 2011, vol. 43, No. 6, pp. 747-753; original document (Year: 2011).*
Jeon, H. et al. translation of full document (26 pages), Korean J. Food Sci. Technol., "Hair Growth Promoting Effect of Black Soybean Extract In Vitro and In Vivo", 2011, vol. 43, No. 6, pp. 747-753 (Year: 2011).*
Murata et al., J. Nat. Med., "Inhibitory activities of Puerariae Flos against testosterone 5alpha-reductase and its hair growth promotion activities", 2012, vol. 66, pp. 158-165 (Year: 2012).*
Yang, Y. et al., Chromatographia, "Ultrasound-Assisted Extraction of Soyasaponins from Hypocotyls, and Analysis by LC-ESI-MS", 2007, vol. 65, No. 9/10, pp. 555-560 (Year: 2007).*
International Search Report for PCT/KR2016/010893, dated Jan. 13, 2017, 5 pages.
Written Opinion of the ISA for PCT/KR2016/010893, dated Jan. 13, 2017, 5 pages.

* cited by examiner

*Primary Examiner* — Shaojia A Jiang
*Assistant Examiner* — Bahar Craigo
(74) *Attorney, Agent, or Firm* — Nixon & Vanderhye P.C.

(57) ABSTRACT

The present invention relates to a composition for improving scalp condition and/or promoting hair restoration containing soyasaponin or a derivative thereof, which can be widely used as an external skin preparation for improving scalp condition and/or promoting hair growth and hair restoration, a cosmetic composition or a pharmaceutical composition, as the composition has high stability for skin without side effects, improves a scalp condition, and is effective in promoting hair growth and/or preventing hair loss by activating stem cells.

4 Claims, 2 Drawing Sheets

[FIG. 1]
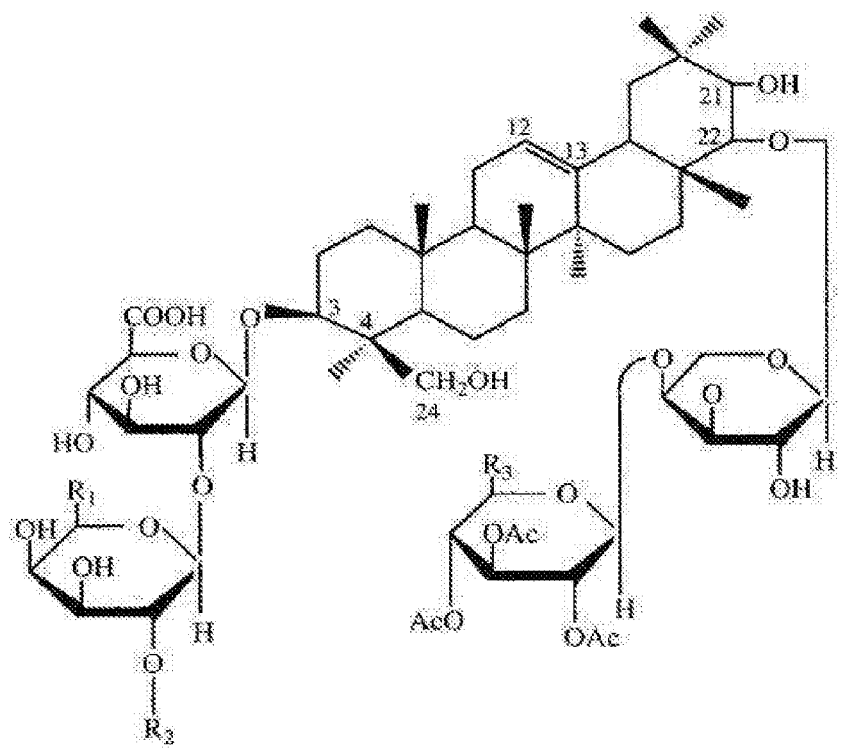
|  | R₁ | R₂ | R₃ |
|---|---|---|---|
| soyasaponin Aa (A4) | $CH_2OH$ | β-D-Glc | H |
| soyasaponin Ab (A1) | $CH_2OH$ | β-D-Glc | $CH_2OAc$ |
| soyasaponin Ac | $CH_2OH$ | α-L-Rha | $CH_2OAc$ |
| soyasaponin Ad | H | β-D-Glc | $CH_2OAc$ |
| soyasaponin Ae (A5) | $CH_2OH$ | H | H |
| soyasaponin Af (A2) | $CH_2OH$ | H | $CH_2OAc$ |
| soyasaponin Ag (A6) | H | H | H |
| soyasaponin Ah (A3) | H | H | $CH_2OAc$ |

[FIG. 2]
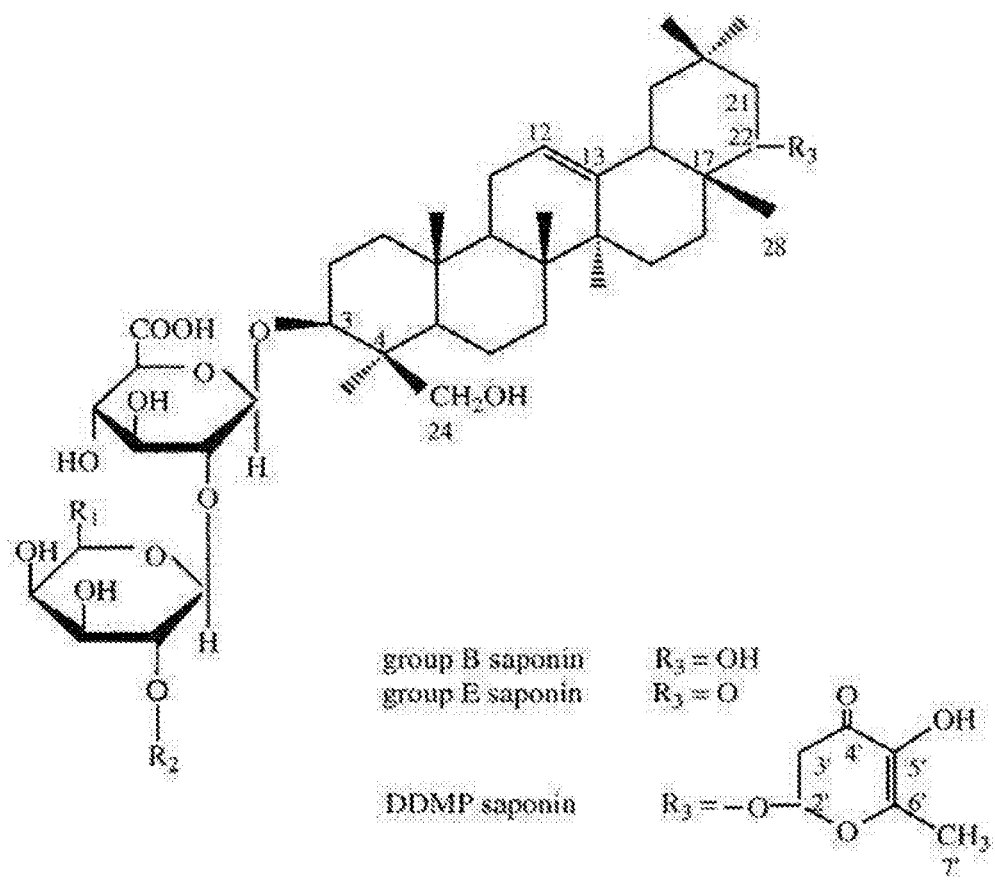

HAIR RESTORATION AND/OR HAIR GROWTH PROMOTING COMPOSITION CONTAINING SOYASAPONIN

This application is the U.S. national phase of International Application No. PCT/KR2016/010893 filed Sep. 29, 2016, which designated the U.S. and claims priority to KR Patent Application Ser. No. 10-2015-0137532 filed Sep. 30, 2015, the entire contents of each of which are hereby incorporated by reference.

TECHNICAL FIELD

The present invention relates to a composition for promoting hair growth and/or hair restoration containing soyasaponin or a derivative thereof, wherein the composition has high stability for skin without side effects and is effective in promoting hair growth and/or preventing hair loss by activating hair follicle stem cells, and thus can be widely used as an external skin preparation for promoting hair growth and hair restoration, a cosmetic composition or a pharmaceutical composition.

BACKGROUND ART

Recently, due to environmental pollution, westernized dietary habits, such as instant food, frequent perming and dying of hair and the like in addition to an increase in social stress, the population with hair loss is gradually increasing. The cycle of hair growth can be divided into anagen stage during which the hair grows, catagen stage during which the hair growth ends and the hair bulb shrinks, telogen stage during which the dermal papilla stops its activity and the hair is retained in the scalp, and exogen stage during which the dermal papilla starts its activity or new hair grows, resulting in shedding of old hair.

Anagen Stage (2 to 7 years) is the period during which the hair grows, and is divided into two stages of producing hair which grows outwards from the bulb into hair follicles and generating hard keratins in the hair follicles. The hair continues to grow itself until the catagen stage.

Catagen Stage (2 to 3 weeks) is the period during which the growth ceases and the metabolism slows down while maintaining the shape of the hair, and keratin is not produced at this stage. The catagen stage accounts for 1% of total hair growth. At this stage, the hair bulb shrinks and divides into dermal papilla, and is surrounded by hair follicles and raises upwards, and the cell division is in a stopped state.

Telogen Stage (3 months) is the period during which the dermal papilla shrinks and the hair follicle gradually shrinks, and the hair root crawls upwards and falls out. It is the period of hair loss until the next stage of growth and lasts for 3 to 4 months.

Normal people have hair mostly in the anagen stage, but people with alopecia have hair mostly in the telogen stage, and thus a phenomenon of hair loss is visible with naked eye. As the hair loss progresses, the period of the anagen stage is shortened, resulting gradual miniaturization of hair. Accordingly, in order to treat the hair loss, it is important to allow the hair follicle in the telogen stage to enter rapidly to the anagen stage and to prolong the anagen stage.

Male-pattern alopecia is a phenomenon which occurs due to the male hormone testosterone, and when the testosterone is converted to dihydrotestosterone (DHT), which is a more stronger hormone, by 5α-reductase, this hormone acts on the hair follicle to induce the hair follicle from the anagen stage to the telogen stage, thereby causing hair loss. Accordingly, a method of inhibiting the production of DHT by 5α-reductase is mainly used to treat male-pattern alopecia.

Female-pattern alopecia is caused mainly by a decrease in the amount of estrogen after menopause. Minoxidil or estrogen are mainly used as therapeutic agents for female-pattern alopecia.

Alopecia areata is caused by an autoimmune disease, mental stress or genetic predisposition. The cause of the alopecia areata is fundamentally different from those of androgenetic alopecia, and as the treatment method is also different, methods of subjecting to adrenocortical hormone therapy, or methods of applying minoxidil to the affected area or artificially inducing stimulation to the affected area are used.

For such various and complex causes of hair loss, the components for promoting blood circulation, inhibiting male hormone function, strengthening the function of hair follicle, etc., are sold as commercialized products. However, none of them has shown a definite effect, and the problem of side effects is often raised. For example, it has been reported that minoxidil had sticky feeling of use and had side effects for causing irritation to the skin. In the case of finasteride, it is currently used as a preparation for oral administration, but adverse effects, such as sexual dysfunction, have been reported according to its consumption, and it was inconvenient to use because it is expected to be effective only by oral administration.

PRIOR ART DOCUMENT

Patent Document

1. Korean Patent No. 10-0616342 (published on Aug. 29, 2006)

DISCLOSURE

Technical Problem

Substances that are conventionally used for promoting hair growth have many side effects and are inconvenient to use. Thus, in order to solve these problems, the present inventors have conducted intensive studies to find a substance having high stability while having fewer side effects and having less constraints of usage, and found that soyasaponin can provide such effects, thereby completing the present invention.

Accordingly, it is one object of the present invention to provide a composition capable of exhibiting excellent hair growth and hair restoration effects by containing soyasaponin or a derivative thereof.

Technical Solution

In order to achieve the object above, the present invention provides a composition for improving scalp condition and promoting hair restoration, comprising soyasaponin or a derivative thereof as an active ingredient.

The present invention also provides use of soyasaponin or a derivative thereof as a promoting agent for hair growth and/or restoration in the preparation of a composition for external skin preparation (specifically, a cosmetic composition or a pharmaceutical composition).

Advantageous Effects

The soyasaponin used in the present invention is a natural compound present in plants and is used as medicinal herbs.

Thus, it can be applied to the skin without side effects and can provide excellent effects in promoting hair growth or preventing hair loss by activating hair follicle stem cells.

BRIEF DESCRIPTION OF DRAWINGS

FIG. 1 shows the structure of group A soyasaponin.
FIG. 2 shows group B soyasaponin, group E soyasaponin, and DDMP soyasaponin.

DETAILED DESCRIPTION OF THE EMBODIMENTS

The present invention relates to a composition for improving scalp condition and promoting hair restoration, comprising soyasaponin or a derivative thereof as an active ingredient.

Saponins are a glycoside compound found in plant species and have a structure in which at least one saccharide molecule is bound to aglycone such as steroid or triterpenoid, and it is known that about 500 kinds of plants contain saponin. Even in soybeans many kinds of saponins are present, and soyasaponin, which is a soybean saponin, has a complex and diverse molecular structure based on the aglycone structure. Specifically, soyasaponin is largely classified into group A soyasaponin, group B soyasaponin, and group E soyasaponin according to soyasapogenol A represented by Chemical Formula 1 below, soyasapogenol B represented by Chemical Formula 2 below, and soyasapogenol E represented by Chemical Formula 3 below, respectively. The group A soyasaponin is a bisdesmoside saponin in which saccharide chains are bound at two positions of C-3 and C-22, whereas the group B soyasaponin and group E soyasaponin are monodesmoside saponins in which a saccharide chain is bound at one position of C-3. Further, the group B soyasaponin is divided into the one in which DDMP (2,3-dihydro-2,5-dihydroxy-6-methyl-4H-pyran-4-one) is bound at the C-22 position, and the one in which no DDMP is bound. Among them, the one in which DDMP is bound may be classified as a DDMP soyasaponin apart from the group B soyasaponin.

[Chemical Formula 1]

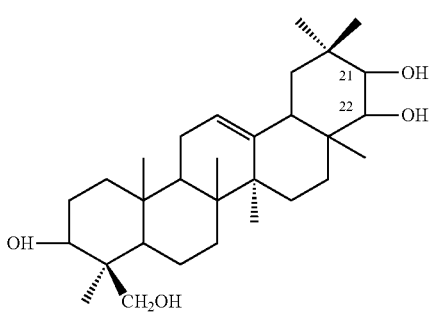

[Chemical Formula 2]

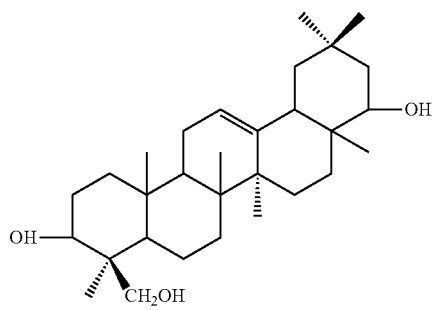

[Chemical Formula 3]

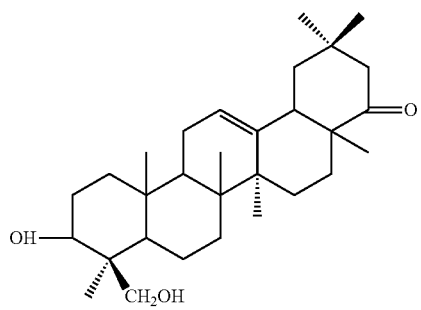

In addition, depending on the scholar soyasaponin compounds corresponding to the group A soyasaponin may be classified as soyasaponin Aa, Ab, Ad, Ae, Af and the like, or may be classified as A1 to A6. Moreover, soyasaponin compounds corresponding to the group B soyasaponin in which no DDMP is bound may be classified as soyasaponin Ba, Bb, Bb', Bc and the like, or may be classified as soyasaponin I to V. Recently, as new soyasaponin compounds have been identified, the nomenclature has been expressed a little differently. FIG. 1 shows the structure of the group A soyasaponin, FIG. 2 shows the group B soyasaponin, group E soyasaponin, and DDMP soyasaponin. The soyasaponins shown in FIG. 1 and FIG. 2 can be summarized as shown in Table 1 below.

TABLE 1

| Group of soyasaponin | Name of soyasaponin compound | Molecular structure of soyasaponin | Molecular weight |
|---|---|---|---|
| Group A | soyasaponin Aa (A4) | glc(1→2)gal(1→2)glcUA(1→3)-A-(22←1)ara(3←1)xyl(2,3,4-tri-O-acetyl) | 1364 |
| | soyasaponin Ab (A1) | glc(1→2)gal(1→2)glcUA(1→3)-A-(22←1)ara(3←1)glc(2,3,4,6-tetra-O-acetyl) | 1436 |
| | soyasaponin Ac | rha(1→2)gal(1→2)glcUA(1→3)-A-(22←1)ara(3←1)glc(2,3,4,6-tetra-O-acetyl) | 1420 |

TABLE 1-continued

| Group of soyasaponin | Name of soyasaponin compound | Molecular structure of soyasaponin | Molecular weight |
|---|---|---|---|
| | soyasaponin Ad | glc(1→2)ara(1→2)glcUA(1→3)-A-(22←1)ara(3←1)glc(2,3,4,6-tetra-O-acetyl) | 1390 |
| | soyasaponin Ae (A5) | gal(1→2)glcUA(1→3)-A-(22←1)ara(3←1)xyl(2,3,4-tri-O-acetyl) | 1202 |
| | soyasaponin Af (A2) | gal(1→2)glcUA(1→3)-A-(22←1)ara(3←1)glc(2,3,4,6-tetra-O-acetyl) | 1274 |
| | soyasaponin Ag (A6) | ara(1→2)glcUA(1→3)-A-(22←1)ara(3←1)xyl(2,3,4-tri-O-acetyl) | 1172 |
| | soyasaponin Ah (A3) | ara(1→2)glcUA(1→3)-A-(22←1)ara(3←1)glc(2,3,4,6-tetra-O-acetyl) | 1244 |
| Group B | soyasaponin Ba (V) | glc(1→2)gal(1→2)glcUA(1→3)-B | 958 |
| | soyasaponin Bb (I) | rha(1→2)gal(1→2)glcUA(1→3)-B | 942 |
| | soyasaponin Bc (II) | rha(1→2)ara(1→2)glcUA(1→3)-B | 912 |
| | soyasaponin Bb' (III) | gal(1→2)glcUA(1→3)-B | 796 |
| | soyasaponin Bc' (IV) | ara(1→2)glcUA(1→3)-B | 766 |
| Group DDMP | soyasaponin αg | glc(1→2)gal(1→2)glcUA(1→3)-B-(22←2')-DDMP | 1084 |
| | soyasaponin βg | rha(1→2)gal(1→2)glcUA(1→3)-B-(22←2')-DDMP | 1068 |
| | soyasaponin βa | rha(1→2)ara(1→2)glcUA(1→3)-B-(22←2')-DDMP | 1038 |
| | soyasaponin γg | gal(1→2)glcUA(1→3)-B-(22←2')-DDMP | 922 |
| | soyasaponin γa | ara(1→2)glcUA(1→3)-B-(22←2')-DDMP | 892 |
| Group E | soyasaponin Bd | glc(1→2)gal(1→2)glcUA(1→3)-E | 956 |
| | soyasaponin Be | rha(1→2)gal(1→2)glcUA(1→3)-E | 940 |

\* "A" represents soyasapogenol A, "B" represents soyasapogenol B, "E" represents soyasapogenol E, "glc" represents β-D-glucopyranosyl, "gal" represents β-D-galactopyranosyl, "glcUA" represents β-D-glucuronopyranosyl, "ara" represents α-L-arabinopyranosyl, "rha" represents α-L-rhamnopyranosyl, "xyl" represents β-D-xylopyranosyl, and "DDMP" represents 2,3-dihydro-2,5-dihydroxy-6-methyl-4H-pyran-4-one.

As used herein, the "derivative of soyasaponin" refers to a chemically modified soyasaponin, which means that a substituent has been modified using soyasaponin produced either by isolation from nature or by synthesis.

In the present invention, the soyasaponin can be prepared by isolation from natural materials or by a chemical synthesis method known in the art, and any soyasaponin compounds commercially available can be used.

The composition of the present invention contains, as an active ingredient, soyasaponin, preferably, soyasaponin A or soyasaponin B, more preferably, soyasaponin A, and most preferably, soyasaponin Aa.

The composition of the present invention may contain soyasaponin or a derivative thereof in an amount of 0.001% by weight to 10% by weight based on the total weight of the composition. When it is less than 0.001% by weight, a sufficient hair growth promoting effect cannot be achieved. When it exceeds 10% by weight, safety and formulation stability may be reduced.

The composition of the present invention activates dermal papilla cells and thus promotes the proliferation of the dermal papilla cells by the use of an active ingredient, such as soyasaponin or a derivative thereof, or a *Glycine gracilis* active germinated extract containing the same, thereby increasing the expression of a vascular endothelial growth factor (VEGF), which is a growth factor necessary for transition of hair into the anagen stage and effectively promoting hair production and hair growth.

The composition of the present invention promotes hair growth through such a mechanism and is not involved in promoting hair growth through the regulation of male hormone and/or blood circulation. Thus, it can be effective in improving severe hair loss and female-pattern alopecia which could not be solved by a method of suppressing male hormone or promoting blood circulation.

The composition according to the present invention, for example, can be formulated into a pharmaceutical composition, a cosmetic composition, an external skin preparation composition, a health food composition, or oral composition.

The pharmaceutical composition according to the present invention may further contain a pharmaceutical adjuvant such as a preservative, a stabilizer, a hydrating agent or an emulsifying accelerator, a salt and/or a buffer for controlling osmotic pressure, etc., and other therapeutically useful substances, and may be prepared into various formulations for oral or parenteral administration in accordance with a conventional method.

The formulation for oral administration may include, for example, tablet, pill, hard or soft capsule, liquid, suspension, emulsion, syrup, powder, discutient, fine granule, granule, pellet, or the like. These formulations may include, in addition to the active ingredient, a surfactant, a diluent (e.g., lactose, dextrose, sucrose, mannitol, sorbitol, cellulose and glycine) or a lubricant (e.g., silica, talc, stearic acid and magnesium or calcium salt thereof, and polyethylene glycol). The tablet may include a binder such as magnesium aluminum silicate, starch paste, gelatin, tragacanth, methyl cellulose, sodium carboxymethyl cellulose and polyvinylpyrrolidone, and may optionally include a pharmaceutical additive such as a disintegrant including starch, agar, alginic acid or a sodium salt thereof, an absorbent, a colorant, a flavor, a sweetener, or the like. The tablet may be prepared according to a common mixing, granulation or coating method. Further, the formulation for parenteral administration may include, for example, injection, drops, ointment, lotion, gel, cream, spray, suspension, emulsion, suppository, patch, etc., but is not limited thereto.

The pharmaceutical composition according to the present invention can be administered via parenteral, rectal, topical, transdermal, subcutaneous routes or the like. The pharmaceutical composition according to the present invention can be, for example, administered topically to the scalp.

Determination of the dose of the active ingredient is within the level of those skilled in the art, and the daily dose of a drug will vary depending on various factors, such as the progression of symptoms of a subject, time of onset, age, health condition, complications and the like. For adults, the composition can be typically administered at a dose of 1 μg/kg to 200 mg/kg, preferably, 50 μg/kg to 50 mg/kg by a split-dose method of once to thrice each day, and the dose is not intended to limit the scope of the present invention in any way.

The composition according to the present invention may be a cosmetic composition. The external form of the cosmetic composition contains a cosmetically or dermatologically acceptable medium or base. It may be in any form suitable for topical application, for example, it may be provided in the form of solutions, gels, solids, paste anhydrous products, emulsions obtained by dispersing oil phase in aqueous phase, suspensions, microemulsions, microcapsules, microgranules, or ionic (liposomes) and non-ionic vesicle dispersants, or in the form of cream, skin toner, lotion, powder, ointment, spray or conceal stick, and these compositions may be prepared according to a conventional method in the art. In addition, the composition according to the present invention can be used in the form of foam or as an aerosol composition further containing a compressed propellant.

In particular, the composition according to the present invention may be formulated in the form of shampoo, hair treatment, scalp treatment, hair essence, hair pack, hair cream, hair lotion, hair tonic, general ointment and the like.

When the formulation of the present invention is paste, cream, or gel, the ingredients therein may include animal fiber, vegetable fiber, wax, paraffin, starch, tragacanth, cellulose derivatives, polyethylene glycol, silicon, bentonite, silica, talc, or zinc oxide, etc, as an ingredient for the carrier.

When the formulation of the present invention is powder or spray, the ingredients therein may include lactose, talc, silica, aluminum hydroxide, calcium silicate, or polyamide powder, and particularly, in the case of spray, it may further include a propellant, such as chlorofluorohydrocarbon, propane/butane or dimethyl ester.

When the formulation of the present invention is a solution or an emulsion, the ingredients therein include solvents, solubilizing agents, or emulsifying agents, for example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or sorbitan fatty acid ester, as an ingredient for the carrier.

When the formulation of the present invention is a suspension, the ingredients therein include liquid diluting agents, such as water, ethanol, or propylene glycol, suspending agents, such as ethoxylated isostearyl alcohol, polyoxyethylene sorbitol ester, and polyoxyethylene sorbitan ester, and microcrystalline cellulose, aluminum meta-hydroxide, bentonite, agar, or tragacanth, etc, as an ingredient for the carrier.

The composition of the present invention may further contain, in addition to the above-described components, functional additives and components contained in a general scalp or hair composition. The functional additives may include components selected from the group consisting of water-soluble vitamins, oil-soluble vitamins, polymer peptides, polysaccharides, sphingolipids and seaweeds extracts.

The cosmetic composition of the present invention may further be mixed with components contained in general cosmetic compositions, in addition to the above functional additives, if necessary. The mixing components which can be added additionally may include oil and fat components, humectants, emollient agents, surfactants, organic or inorganic pigments, organic powder, UV absorbents, preservatives, sanitizers, antioxidants, vegetable extracts, pH adjusting agents, alcohols, coloring agents, flavoring agents, blood circulation promoters, cooling agents, adiaphoretics, purified water, or the like.

Further, the present invention relates to an external skin preparation including the composition, and the external skin preparation is a generic term that may include any substances applied to the skin exterior, and cosmetics and medicines of various formulations may be included therein.

Furthermore, the composition of the present invention may be in the form of a health food composition. In the health food composition of the present invention, the composition may be in the form of liquid or solid, and may be in the form of tablets, capsules, soft capsules, pills, granules, beverages (drinks), diet bars, chocolates, caramel or in confectionery formulations, but is not limited thereto. The health food composition of the present invention may appropriately contain excipients, saccharides, flavoring agents, coloring agents, oils and fats, proteins, and the like, as needed, in addition to the above active ingredients.

In addition, the composition of the present invention may contain a skin absorption promoting substance to increase the effects of improving scalp condition and promoting hair restoration.

DETAILED DESCRIPTION OF THE EMBODIMENTS

Hereinafter, the constitution and effects of the present invention will be described in more detail by way of Experimental Examples and Preparation Examples. However, these Experimental Examples and Preparation Examples are given for illustrative purposes only, and the scope of the invention is not intended to be limited by these Examples

[Reference Example 1] Preparation of Soyasaponin

In order to test the efficacy of the composition of the present invention, soyasaponin Aa was purchased from Chengdu Biopurity Phytochemicals Ltd., and used.

[Experimental Example 1] Evaluation of Expression of Hair Growth Factor VEGF in Dermal Papilla Cells In order to evaluate the degree of expression of vascular endothelial growth factor (VEGF) which is a growth factor necessary for transition of hair into the anagen phase as a growth factor necessary for angiogenesis by soyasaponin Aa, an in vitro system was applied to treat the soyasaponin Aa, and the activity thereof was evaluated. For the experiment, $4 \times 10^5$ dermal papilla cells (DPC) (P.11) of a 47-year-old male was seeded in a 12-well plate and cultured in DMEM (Dulbecco's modified Eagle's medium; GibcoBRL, Gaithersburg, Md., USA) containing 10% FBS (fetal bovine serum) overnight. After the culture, the cells were treated with soyasaponin Aa at 20 ppm. DMSO was used as a negative control. After 24 hours, the mixing solution with treated soyasaponin Aa was collected, and the degree of VEGF expression by the soyasaponin Aa was confirmed using VEGF ELISA (Vascular endothelial growth factor Enzyme-Linked Immunosorbent Assay; R&D biosystems). The results are shown in Table 2.

TABLE 2

| Samples | VEGF (ng/ml) in culture medium |
|---|---|
| Soyasaponin Aa (20 ppm) | 16.7 |
| Control | 4.3 |

As shown in Table 2, the soyasaponin Aa significantly increased the expression of hair growth factor VEGF by approximately 4 times or more in the dermal papilla cells as compared to the control group, thereby confirming that it showed a significant difference in terms of the degree of VEGF expression.

Accordingly, it was confirmed that the soyasaponin Aa according to the present invention has an excellent hair production promoting ability.

[Experimental Example 2] Evaluation of Proliferation Effect on Hair Follicle Dermal Papilla Cells Keratin proteins constituting the hair are produced in the keratinocytes of the hair root, and the keratinocytes are differentiated from the dermal papilla cells. Therefore, if soyasaponin Aa according to the present invention promotes the activity of the dermal papilla cells, it can promote the activity of the keratinocytes differentiated therefrom, and further can promote the hair production.

In the experiment, the promoting effect of soyasaponin Aa on the activity of dermal papilla cells was evaluated as follows:

First, in the present invention, a human dermal papilla cell line was used (obtained from Prof. Kwan Oh Sang of dermatology in Seoul National University Hospital). The cell line was cultured for 24 hours in an incubator maintained at 5% $CO_2$, 37° C. using DMEM (Dulbecco's modified Eagle's medium; Gibco BRL, Gaithersburg, Md., USA) containing 10% FBS, and then independently treated with soyasaponin Aa at 1 ppm, 10 ppm, and 20 ppm. DMSO was used as a negative control. Cell proliferation (%) was measured using a WST-1 kit (Roche) 24 hours after the treatment with the test materials. The results are shown in Table 3 below.

TABLE 3

| Test materials | hDPc proliferation (%) |
|---|---|
| Soyasaponin Aa (20 ppm) | 172 |
| Soyasaponin Aa (10 ppm) | 145 |
| Soyasaponin Aa (1 ppm) | 119 |
| Control | 100 |

As shown in Table 3, the soyasaponin Aa according to the present invention significantly increased the proliferation of both cells at 10 ppm and 20 ppm. In particular, the cells treated with soyasaponin Aa at 20 ppm showed a rate of increase in the dermal papilla cell proliferation of about 1.7 times or more compared with the control group. This means that the soyasaponin Aa according to the present invention can promote the proliferation of dermal papilla cells and can more effectively promote the activity of keratinocytes and hair production.

[Experimental Example 3] Evaluation of Hair Growth Promoting Effect Using Human Hair Follicle Organ An experiment was conducted to confirm the hair growth promoting ability in the actual human hair follicle organ of the present invention.

The hair follicle organ was isolated from the scalp tissue of the occipital region of a 55-year-old male one at a time, and cultured in William's E medium (containing L-glutamine (2 mM), insulin (10 μg/ml), hydrocortisone (40 ng/ml), antibiotics (1%) antimycotic (1%)).

The hair follicles grown on the third day after culturing were selected and cut into 3 mm. As for the selected hair follicle tissues, those without drug treatment were used as a control group, and the hair follicle tissues were each treated with soyasaponin Aa at 1 ppm, 5 ppm, and 10 ppm. Then, the hair length was measured 8 days after the treatment. The results are shown in Table 4 below.

TABLE 4

| Samples | Average growth length (mm) |
|---|---|
| Soyasaponin Aa (10 ppm) | 2.46 |
| Soyasaponin Aa (5 ppm) | 2.05 |
| Soyasaponin Aa (1 ppm) | 1.71 |
| Control | 1.64 |

As a result, as shown in Table 4, the hair follicle tissues treated with soyasaponin Aa had the hair growth promoting effect superior to that of the control group in terms of the increase in hair length in the hair follicle organ. In particular, when 10 ppm of soyasaponin Aa was treated, it showed that the hair length growth effect was superior by 1.5 times compared to the control group.

Accordingly, the results of Table 4 showed that the soyasaponin Aa according to the present invention has an excellent effect in promoting the growth of hair length in the hair follicles.

[Formulation Example 1] Hair Tonic

A hair tonic was prepared in a conventional manner according to the composition shown in Table 5 below.

TABLE 5

| Ingredients | Weight ratio (%) |
|---|---|
| Ethanol | 50 |
| Menthol | 0.02 |
| Glycerin | 3 |
| Salicylic acid | 0.05 |
| Soyasaponin Aa | 0.5 |
| Flavoring and coloring agents | Suitable amount |
| Purified water | Balance (to 100) |

[Formulation Example 2] Hair Lotion

A hair lotion was prepared in a conventional manner according to the composition shown in Table 6 below.

TABLE 6

| Ingredients | Weight ratio (%) |
| --- | --- |
| Cetostearyl alcohol | 2.0 |
| EDTA 2Na | 0.2 |
| Hydroxyethyl cellulose | 0.5 |
| Mineral oil | 5.0 |
| Soyasaponin Aa | 1.0 |
| Preservatives | Suitable amount |
| Flavoring and coloring agents | Suitable amount |
| Purified water | Balance (to 100) |

[Formulation Example 3] Hair Nutritive Cosmetic Water

A hair nutritive cosmetic water was prepared in a conventional manner according to the composition shown in Table 7 below.

TABLE 7

| Ingredients | Weight ratio (%) |
| --- | --- |
| Wax | 4.0 |
| Polysorbate 60 | 1.5 |
| Sorbitan sesquioleate | 0.7 |
| Mineral oil | 10.0 |
| Glycerin | 3.0 |
| Butylene glycol | 3.0 |
| Propylene glycol | 3.0 |
| Carboxyvinyl polymer | 0.1 |
| Triethanolamine | 0.2 |
| Soyasaponin Aa | 1.5 |
| Preservatives | Suitable amount |
| Flavoring and coloring agents | Suitable amount |
| Purified water | Balance (to 100) |

[Formulation Example 4] Hair Shampoo

A hair shampoo was prepared in a conventional manner according to the composition shown in Table 8 below.

TABLE 8

| Ingredients | Weight ratio % |
| --- | --- |
| Purified water | Balance (to 100) |
| Soyasaponin Aa | 5.0 |
| Sodium lauryl sulfate | 36.0 |
| Cocamidopropyl betaine | 8.0 |
| Palmitic malate | 2.0 |
| Glycol Stearate | 1.5 |
| Polyquaternium 10 | 0.5 |
| Citric acid | 0.1 |
| Glycerin | 2.0 |
| Preservatives, flavoring and coloring agents | Suitable amount |

[Formulation Example 5] Hair Conditioner

A hair conditioner was prepared in a conventional manner according to the composition shown in Table 9 below.

TABLE 9

| Ingredients | Weight ratio (%) |
| --- | --- |
| Purified water | Balance (to 100) |
| Soyasaponin Aa | 1.0 |
| Propylene glycol | 2.0 |
| Cetyltrimethylammonium chloride | 1.0 |
| Cetyl alcohol | 3.0 |
| Stearyl alcohol | 3.0 |
| Mineral oil | 0.5 |
| Citric acid | 0.2 |
| Polydimethylsiloxane | 1.0 |
| Preservatives, flavoring and coloring agents | Suitable amount |

[Formulation Example 6] Ointment

An ointment was prepared in a conventional manner according to the composition shown in Table 10 below.

TABLE 10

| Ingredients | Weight ratio (%) |
| --- | --- |
| Purified water | Balance (to 100) |
| Glycerin | 8.0 |
| Butylene glycol | 4.0 |
| Liquid paraffin | 15.0 |
| Beta glucan | 7.0 |
| Carbomer | 0.1 |
| Soyasaponin Aa | 10.0 |
| Caprylic capric triglyceride | 3.0 |
| Squalene | 1.0 |
| Cetearyl glucoside | 1.5 |
| Sorbitan stearate | 0.4 |
| Stearyl alcohol | 1.0 |
| Preservatives | Suitable amount |
| Flavoring agent | Suitable amount |

[Formulation Example 7] Soft Capsule Formulation 50 mg of soyasaponin Aa, 80 to 400 mg of L-carnitine, 180 mg of soybean oil, 2 mg of palm oil, 8 mg of vegetable hydrogenated oil, 4 mg of yellow wax, and 6 mg of lecithin are mixed and filled at 400 mg per capsule according to a conventional method to prepare a soft capsule.

[Formulation Example 8] Tablet Formulation 50 mg of soyasaponin Aa, 200 mg of galactooligosaccharide, 60 mg of lactose, and 140 mg of maltose are mixed and granulated using a fluidized bed drier, and then 6 mg of sugar ester was added and subjected to tableting to prepare a table formulation.

[Formulation Example 9] Granule Formulation 50 mg of soyasaponin Aa, 250 mg of anhydrous crystalline glucose, and 550 mg of starch are mixed and granulated to form granules using a fluidized bed granulator, and then filled into capsules.

[Formulation Example 10] Drinking Formulation 50 mg of soyasaponin Aa, 10 g of glucose, 0.6 g of citric acid, and 25 g of liquid oligosaccharide are mixed, and then 300 ml of purified water is added thereto, and the mixture is filled into a bottle. Then, the beverage was prepared by sterilizing at 130° C. for 4 to 5 seconds.

Although specific parts of the present invention have been described in detail, it will be apparent to those skilled in the art that these specific techniques are merely a preferred embodiment and that the scope of the present invention is not limited thereto. Therefore, the substantial scope of the present invention will be defined by the accompanying claims and their equivalents.

The invention claimed is:

1. A method of promoting hair growth or hair restoration of a subject comprising:
   topically applying a composition containing soyasaponin Aa as a sole effective promoting agent for hair growth or hair restoration to the skin of the subject.
2. The method of claim 1, wherein the soyasaponin Aa is contained in an amount of 0.001% by weight to 10% by weight based on the total weight of the composition.
3. The method of claim 1, wherein the composition delays the regression of the hair follicle cells.
4. The method of claim 1, wherein the composition promotes the proliferation of dermal papilla cells.

* * * * *